US006454711B1

(12) United States Patent
Haddad et al.

(10) Patent No.: US 6,454,711 B1
(45) Date of Patent: Sep. 24, 2002

(54) MICROWAVE HEMORRHAGIC STROKE DETECTOR

(75) Inventors: Waleed S. Haddad, Dublin; James E. Trebes, Livermore, both of CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/298,342

(22) Filed: Apr. 23, 1999

(51) Int. Cl.$^7$ ............................................. A61B 25/00
(52) U.S. Cl. .................. 600/371; 600/407; 600/430; 600/504
(58) Field of Search ................... 600/407, 430, 600/504, 481, 371

(56) References Cited

U.S. PATENT DOCUMENTS

| | | | | |
|---|---|---|---|---|
| 4,307,726 A | | 12/1981 | Paulson et al. ............. | 128/653 |
| 4,690,149 A | * | 9/1987 | Ko ............................. | 600/546 |
| 6,064,903 A | * | 5/2000 | Riechers et al. ............ | 600/407 |
| 6,233,479 B1 | * | 5/2001 | Haddad et al. ............. | 600/430 |

OTHER PUBLICATIONS

Riechers R G et al: "Microwave detection system for locating hemorrhage sites within the cranium and other regons" 15$^{th}$ Annual AESS/IEEE Dayton Section Symposium. Sensing the Wold: Analog Sensors and Systems across the Spectrum (Cat. No.98EX178), 15$^{th}$ Annual AESS/IEEE Dayton Section Symposium. Sensing the World: Analog Sensors and Systems across the Spectrum, FA, pp. 1–12, XP000900732 1998, New York, NY USA, IEEE, USA ISBN: 0–7803–9.

* cited by examiner

Primary Examiner—Robert L. Nasser
(74) Attorney, Agent, or Firm—John P. Woodridge; Alan H. Thompson (57) ABSTRACT

The microwave hemorrhagic stroke detector includes a low power pulsed microwave transmitter with a broad-band antenna for producing a directional beam of microwaves, an index of refraction matching cap placed over the patients head, and an array of broad-band microwave receivers with collection antennae. The system of microwave transmitter and receivers are scanned around, and can also be positioned up and down the axis of the patients head. The microwave hemorrhagic stroke detector is a completely non-invasive device designed to detect and localize blood pooling and clots or to measure blood flow within the head or body. The device is based on low power pulsed microwave technology combined with specialized antennas and tomographic methods. The system can be used for rapid, non-invasive detection of blood pooling such as occurs with hemorrhagic stroke in human or animal patients as well as for the detection of hemorrhage within a patient's body.

60 Claims, 4 Drawing Sheets

MICROWAVE HEMORRHAGIC STROKE DETECTOR

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to the detection of the presence of blood pooling or blood flow within the body and within the head, and more specifically, it relates to the diagnosis of stroke.

2. Description of Related Art

The are two forms of stroke: hemorrhagic and ischemic. Hemorrhagic stroke is caused by internal bleeding within the brain. Ischemic stroke is caused by blockage of a blood vessel that feeds the brain or a region of the brain. A stroke attack can occur suddenly and with little or no warning, and can result in severe physical impairment or death. Due to the rapid timescale for potentially severe or fatal damage to the brain these must be treated as rapidly as possible. Surgical intervention can be used to treat hemorrhagic stroke. An anti-clotting agent can be used to treat ischemic stroke. Unfortunately applying an anticlotting agent in the case of hemorrhagic stroke can cause fatal internal bleeding within the brain. At present, there is no non-invasive way to check patients for, and to differentiate between hemorrhagic and ischemic stroke other than computed tomography (CT) and magnetic resonance imaging (MRI).

The cost of computed tomography and magnetic resonance imaging is high. A typical head scan is about $500–$800, and can cost much more if the patient must be sedated or closely monitored during the scan. In many cases, several scans of a single patient are necessary to monitor the development of his/her condition.

The total time required for a scan is about 15 minutes using a helical scan device (faster than the standard CT scanners). If the scanner is physically located right in the emergency room, this time can go down to 5–10 minutes. However, the actual time to diagnose a brain hemorrhage (or other problem) is usually limited by patient transportation, preparation and the need to have a radiologist read the scan. If the scan must be sent out of the emergency room for reading, the overall time can be between 30 minutes and 3 hours.

SUMMARY OF THE INVENTION

It is an object of the present invention to provide a microwave hemorrhagic stroke detector that is a low cost, non-invasive, portable device for screening patients for the presence, approximate location, approximate size and rate of internal bleeding within the brain.

It is another object of the present invention to provide a microwave blood flow detector.

Still another object of the invention is to use microbubbles as a contrast agent for microwave imaging of blood flow and hemorrhage.

The microwave hemorrhagic stroke detector can be used at the scene of the injury or stroke incident by the paramedic or first responder in a properly equipped ambulance, in the emergency room (ER), in local clinics and in hospital intensive care units (ICU) and operating rooms (OR). It allows rapid testing of patients prior to CT or MRI scanning, eliminating unnecessary scans, or can replace the use of CT for examining some patients. It has the potential for saving many lives and reducing long term damage to stroke and head injury victims by reducing the time of diagnosis. It also facilitates and reduces the cost of repeated scans to monitor the size and rate of growth of a blood pool within the head. It can greatly reduce the medical costs associated with testing and treating stroke victims, as well as reducing the costs of patient rehabilitation and convalescence by reducing the morbidity resulting from current treatment time delays.

The Microwave Hemorrhagic Stroke Detector is especially beneficial in terms of both cost and time of diagnosis because it can be used for patient screening at the scene of a stroke or in emergency medical centers, providing immediate determination of the nature of the stroke and allowing appropriate, rapid treatment, e.g., surgical intervention or anti clotting drug to be administered.

DETAILED DESCRIPTION OF THE INVENTION

The invention is a low cost, non-invasive, portable device for screening patients for the presence, approximate location, approximate size and rate of the internal bleeding within the brain. The device could be used at the scene of the injury or stroke incident by the paramedic or first responder in a properly equipped ambulance, in the emergency room (ER), in local clinics and in hospital intensive care units (ICU) and operating rooms (OR). It will allow rapid testing of patients prior to CT or MRI scanning, elimininating unnecessary scans, or could possibly replace the use of CT for examining a certain class of patients. It has the potential for saving many lives and reducing long term damage to head injury victims by reducing the time of diagnosis. It will also facilitate and reduce the cost of repeated scans to monitor the size and rate of growth of a blood pool within the head. It will greatly reduce the medical costs associated with testing and treating stroke victims, as well as reducing the costs of patient rehabilitation and convalescence by reducing the morbidity resulting from current treatment time delays.

The microwave hemorrhagic stroke detector includes an array (e.g., a 2-D or 3-D array) of transmitters and receivers in a "tomographic" configuration operating in pulsed mode (pulses ~60–120 ps long, 2–5 GHz center frequency). An adjustable (inflatable with dielectric filling liquid, or other space filling mechanism) form-fitting dielectric matching helmet insert is provided for the patient to place his/her head. This helmet insert may be disposable. A tomography style algorithm produces a map of the dielectric anomalies within the head. A computer system and associated interface electronics are provided for hardware control, data processing and display of data. Some embodiments employ a mechanical rotation system (see FIGS. 1 and 2). Some embodiments utilize a specialized algorithm and software for multiplexing the transmitter/receiver pairs (see FIG. 3 below).

The first embodiment employs a large parabolic transmitter antenna and an array of 4 (or possibly 5) receiver antennas (with parabolic reflectors) which are mounted abreast on a rigid fixture with a small (about 3–5 mm) space (gap) between them. These gaps may be occupied by a septum of microwave absorbing material to help reduce any residual crosstalk between antennas. Directly connected to each of the transmitter antenna and the receiver antennas is a transmitter or receiver circuit card respectively. The transmitter antenna is mounted directly opposite to and facing the receiver array and fixtured to a motor driven mechanical rotation stage. Also affixed to the supporting structure which holds the antennas and directly in contact with them is dielectric filling material. This is designed to allow the antennas to be placed in a linear array, and yet to fill the gap between the antenna array and the circular dielectric helmet insert (see FIG. 7). They are made of the same dielectric filling material as that in the parabolic reflectors and in the dielectric helmet insert. The filling material is placed in intimate contact with the cylindrical helmet insert but is free to slide against its surface, thus allowing the antenna arrays to rotate, while providing a continuous dielectric filling between the antennas and the patient's head. The large parabola and the linear array of straightforward parallel firing antennas is designed to work with approximately collimated beams and is chosen to be optimized for straight ray tomographic geometry.

Figure 1:
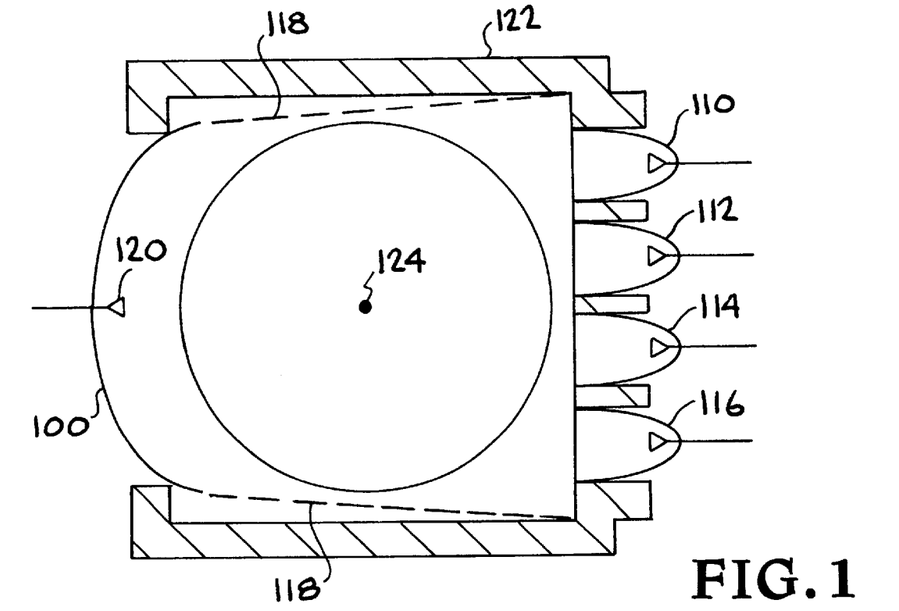
FIG. 1 shows a top crossectional diagram of one embodiment of the hemorrhagic stroke detector employing all parabolic reflector antennas.

FIG. 1 shows a top crossectional diagram of one embodiment of the hemorrhagic stroke detector employing all parabolic reflector antennas. The large parabolic reflector 100 attempts to produce a near plane wave illumination of the object (head) while the small individual parabolas 110, 112, 114, and 116, divide the transmitted wavefront for coarse spatial resolution (e.g., four pixels across). The dotted lines 118 indicate the outer boundaries of the beam transmitted from microwave feed 120. The microwave absorber material 122 and the housing (not shown) provide shielding and act to prevent entry of signals from outside objects. For this embodiment, the entire structure may rotate about the axis of rotation 124 which is centered in the dielectric helmet (and approximately centered on the patient's head). The helmet itself stays stationary. A slip joint between the dielectric helmet and the dielectric filling material allows the device to rotate freely. Swivel connectors are used to allow cables from the antenna feeds to move safely with the rotation of the device.

Figure 2:
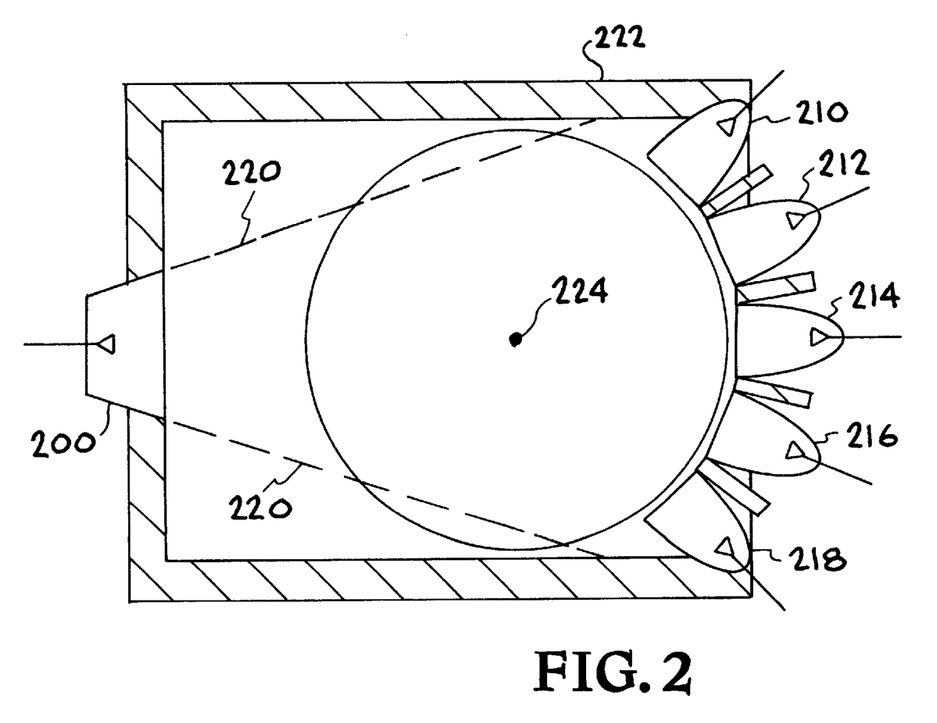
FIG. 2 shows a top crossectional diagram of one embodiment of the hemorrhagic stroke detector employing a wide angle horn transmitter antenna and an array of parabolic reflector receiver antennas.

FIG. 2 shows a top crossectional diagram of one embodiment of the hemorrhagic stroke detector employing a wide angle horn transmitter antenna and an array of parabolic reflector receiver antennas. The wide angle, wide bandwidth horn 200 (standard microwave antenna) produces a diverging wave illumination of the object (head) while the small individual parabolas 210, 212, 214, 216 and 218 divide the transmitted wavefront and provide coarse spatial resolution (five pixels across in this drawing). The dotted lines indicate the outer boundary of the transmitted beam 220. The microwave absorber material 222 and the housing (not shown) provide shielding and prevent entry of signals from outside objects. As in the embodiment discussed above, the entire structure may rotate about the axis of rotation 224 which is centered in the dielectric helmet (and approximately centered on the patient's head). The helmet itself stays stationary. A slip joint between the dielectric helmet and the dielectric filling material allows the device to rotate freely. Swivel connectors are used to allow cables from the antenna feeds to move safely with the rotation of the device.

Figure 3:
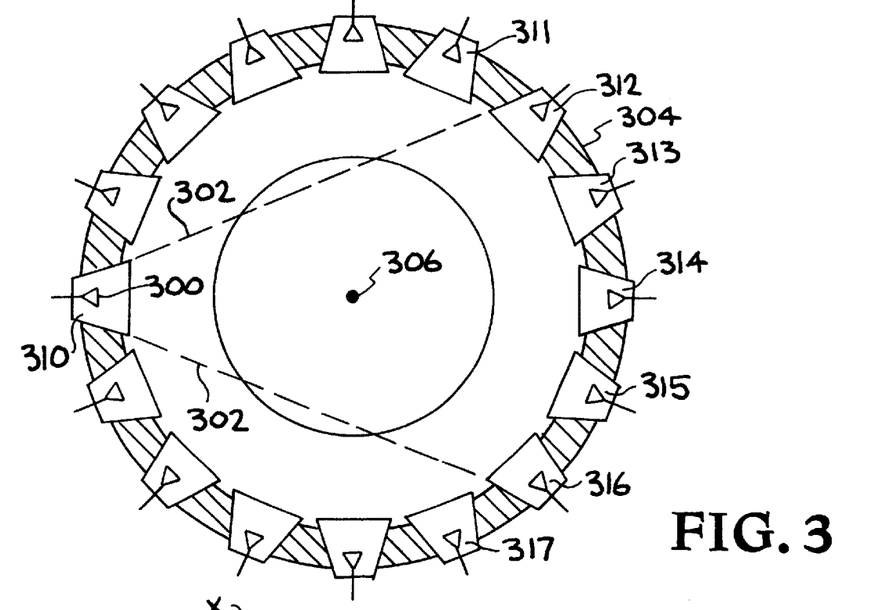
FIG. 3 shows a top crossectional diagram of one embodiment of the hemorrhagic stroke detector employing all wide angle horn antennas.

FIG. 3 shows a top crossectional diagram of one embodiment of the hemorrhagic stroke detector. Microwave feed 300 projects a microwave beam. The dotted lines 302 indicate the boundary of the transmitted beam. The microwave absorber material 304 and the housing (not shown) provide shielding and prevent entry of signals from outside objects. For this embodiment, no rotation or moving parts are required. The tomographic data set is generated by electronically multiplexing the transmitters and receivers such that "projections" of the sample (patient's head) are acquired from several angles about the (virtual) axis of rotation 306. This is done by sequentially using one antenna (e.g., antenna 310) to transmit a pulse while the group of (in this case seven) antennas (311–317), across from it are used to receive portions of the transmitted wavefront. Once each antenna in the circle has been used as a transmitter, the full set of projections will have been recorded.

With respect to the small parabolic reflector receiver antennas, the optimum antenna design is any one which produces a collimated or slightly focused beam pattern with a characteristic width of approximately 5 cm (or less). These antennas should be filled with dielectric material which is the same as that filling the helmet insert that covers the patient's head during data acquisition. Filling the antennas with this material means that the microwave radiation will be launched within the proper dielectric medium for improved coupling (impedance matching) and allows the antenna dimensions to be small enough to meet the requirements of the system since the wavelength of the radiation is $\lambda_0/n_r$, where $\lambda_0=c/v$ and $n_r$ is the real part of the refractive index of the dielectric medium in which the radiation is propagating and $v$ is the frequency of the radiation. A specific example of one such antenna design is as follows. Starting with pulsed microwave radiation with a frequency of 5 GHz, a simple feed antenna with a deep parabolic reflector is chosen. This reflector can be spin pressed out of 1/16" thick A1. The parabolic reflector produces a collimated beam pattern. The shape of the parabola is chosen so that its focus is located 1/4 wavelength (of the microwave radiation) from the vertex. The dipole feed is placed at the focus of the parabola. The aperture and depth of the parabola must be greater than or equal to several wavelengths. The degree of collimation will be affected by the depth of the dish; a deeper dish and larger aperture will produced better collimation.

The parabolic reflector used for the receiver array antennas (embodiments 1 and 2) should be designed such that the microwave feed is located at the focus of the parabola. The equation of a parabola with vertex at the origin is $x^2=4ay$, where a is the distance from the vertex of the parabola to its focus. It is desirable that $a=\lambda/4=c/(4n_r\nu) \rightarrow x^2=yc/(n_r\nu)=\lambda y$, where $\lambda_0$ is the wavelength of the radiation in vacuum, c=speed of light=$3.0\times10^8$ m/s, $n_r$=real part of the refractive index of dielectric filling material, and $\nu$=microwave pulse center frequency. In the case where 5 GHz is selected as the center frequency of the microwave pulse, an optimized antenna design is produced by choosing the overall depth of the parabola's reflector $y_{max}=10\lambda=80$ mm and a dielectric filling with a refractive index of 7.5 to match the tissue. Then $\lambda=8$ mm and the antenna width=$2x_{max}=50.6$ mm=$6\lambda$. An array of 4 antennas will then span a width just over 200 mm which is approximately the diameter of an average human head.

To estimate the time delay for a microwave pulse propagating through normal head versus a head with a small blood pool (due to a hemorrhage),the refractive index n: for blood $n_r \approx 8$, and for the brain $n_r \approx 7.5$. If it is assumed that the nominal diameter of head $\approx 200$ mm=20 cm and it is desired to detect a pool of blood that is about 2 cm. in diameter, then the time of flight (T.O.F.) for the two paths is determined as follows. The T.O.F. for path 1 is $(7.5\times 20$ cm$)/c=5.0$ ns. The T.O.F. for path 2 is $(8.0\times 2$ cm$+7.5\times 18$ cm$)/c=(16$ cm$+135$ cm$)/c=(1.51$ m$)/c=5.033$ ns. The time difference is therefore approximately 33 ps. Since the MIR pulse width can be ~60 ps, the invention could detect a 33 ps time shift in the position of the edge of the pulse. T.O.F. tomography can therefore detect a blood pool of <2 cm diameter.

In time-of-flight (TOF) tomography, a pulse is transmitted through the sample and received at the other side a time later. The total time delay represents the integral of the real part of the refractive index (ratio of speed of light in the medium to speed in vacuum) over all points along the path traveled by the pulse between the transmitter and receiver. Since tomography is based on reconstructing an image (or in this case a low resolution image we call a map) from a set of path integrals, the refractive index map of the sample can be reconstructed from the TOF information recorded from many different angles.

Figure 9:
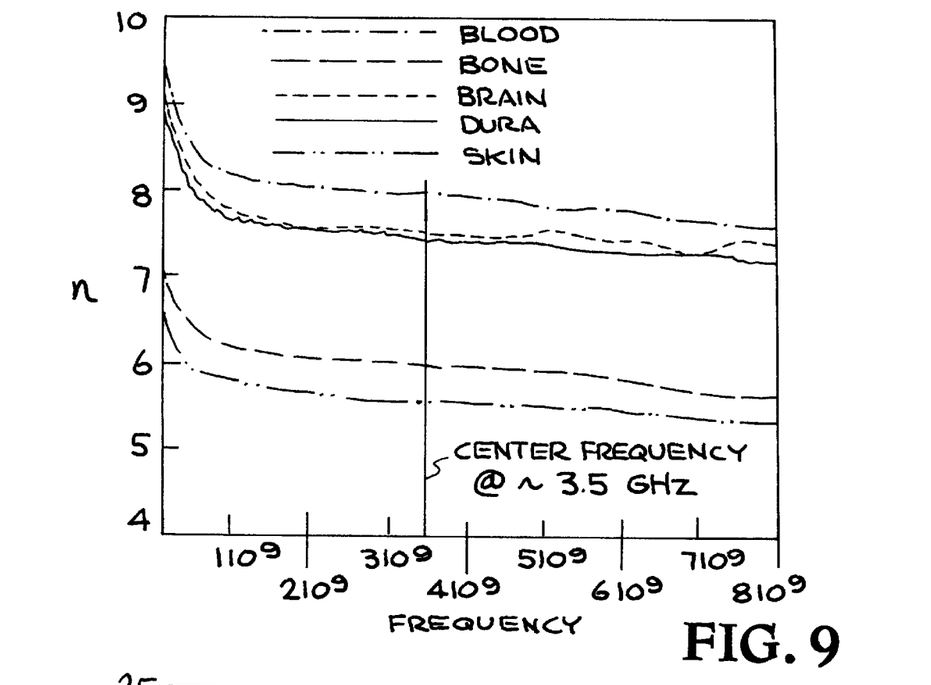
FIG. 9 plots the real refractive index in the various tissue components of the head over a wide range of microwave frequencies.
Figure 10:
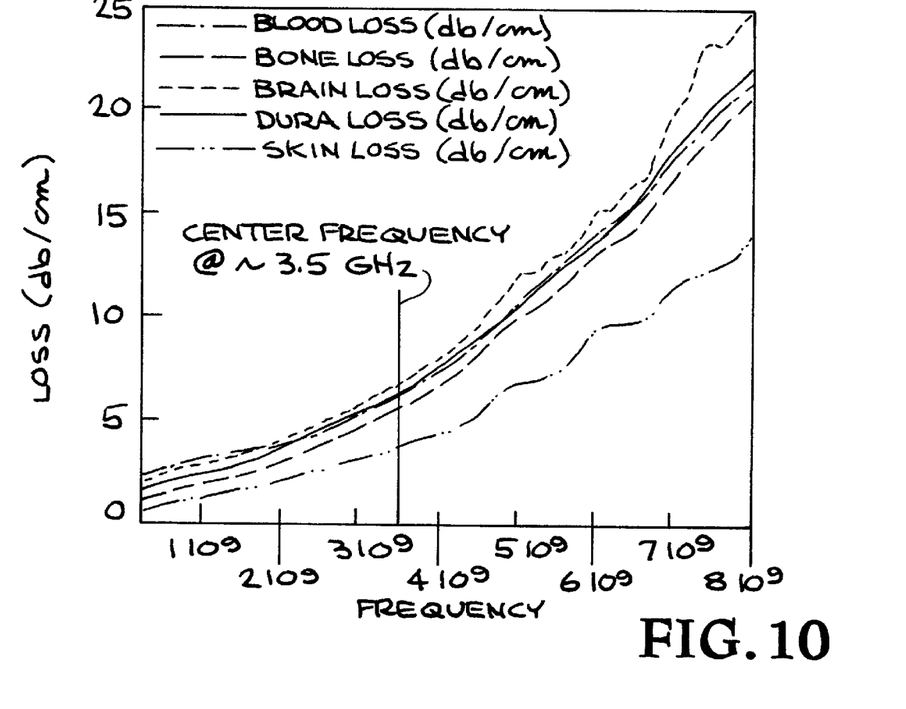
FIG. 10 plots the loss due to absorption in the various tissue components of the head over a wide range of microwave frequencies.

Natural contrast exists between blood and brain tissue at microwave frequencies due primarily to differences in the real part of the refractive index (which represents the propagation velocity or "speed of light" in the medium). The attenuation of the microwave energy in the frequency range used by MIR devices is, however, relatively low, allowing the required transmission mode measurements to be made. The real refractive index and loss due to absorption in the various tissue components of the head are plotted in FIGS. 9 and 10 respectively, over a wide range of microwave frequencies.

Special contrast for mapping cerebral blood flow can be obtained by the injection of microbubbles as a contrast agent which is administered to the patient just prior to data acquisition with the microwave head mapping system. Microbubble contrast agents suitable for this flow mapping have been developed for use with medical ultrasound imaging. These microbubble contrast agents have been approved for clinical use and are commercially available (such as Echogen™). The data acquisition and mapping reconstruction can be done very quickly—between 5 and 30 seconds, depending on the exact configuration of the system. Cerebral blood flow can be mapped by conducting dynamic studies, i.e. administering a bolus of the contrast agent of known volume, then acquiring and reconstructing the mapping after a timed delay. Alternatively, a sequence of maps can be generated at certain time intervals after administration of the contrast agent. The differences between the blood content from one map to the next in the sequence can then be used to quantitatively determine the flow. Microbubble agents may be used for contrast enhancement in microwave mapping of blood flow within the body.

In this particular case, because the wavelength of the radiation is relatively large and the antenna apertures, and therefore the spatial resolution of the system, are large (~50 mm), dielectric anomalies of interest may only intercept a portion of the wavefront reaching a particular receiver element (see diagram in FIG. 2). In addition, due to varying absorption of the medium with frequency, the broadband pulse may become distorted in shape (in the time domain) by the time it traverses the sample. These factors necessitate a special type of algorithm, for processing the data prior to using standard tomographic reconstruction methods to generate the map.

Prior knowledge of the properties of a "normal" sample can be used to filter signals so that the recorded time delay information can be properly used. The information about the normal sample is obtained from laboratory experiments and clinical trials.

Once the transmitted signals have been recorded, they are pre-processed to suppress the effects of the transmitted pulse shape (because it is not a delta function). This can be done by calculating for each receiver $$S_i^\theta(t)_{meas} = \int_0^{\tau_{max}} R_i^\theta(\tau)_{meas} T(\tau-t)d\tau$$

where
$R_i^\theta(t)$
represents the signal (a function of time t) recorded by the ith receiver from the angular position $\theta$, and
$T(t)$
is the transmitted pulse wave form (also a function of time t), and
$S_i^\theta(t)_{meas}$
is the processed measured signal recorded by the ith receiver from the angular position $\theta$, and $$\tau_{max} = \frac{xn_{max}}{c}$$

is the maximum time of flight expected along the longest possible path, with $n_{max}$
being the maximum expected value for the refractive index anywhere within between the transmitters and receivers. The integral above is similar to what is known as range compression in synthetic aperture radar (SAR) imaging.

Next, the normal or "standard" signal is calculated and stored in the memory of the controlling computer system $$S_i^\theta(t)_{norm} = \int_0^{\tau_{max}} R_i^\theta(\tau)_{norm} T(\tau-t)d\tau$$

The above integrals, as well as all other calculations, are performed numerically in the actual system, and therefore are actually calculated as discrete sums. Because of the low spatial resolution of the system, and therefore of the reconstructed map, the sums can be performed over only a few large time steps and will be calculated very quickly.

Figure 4:
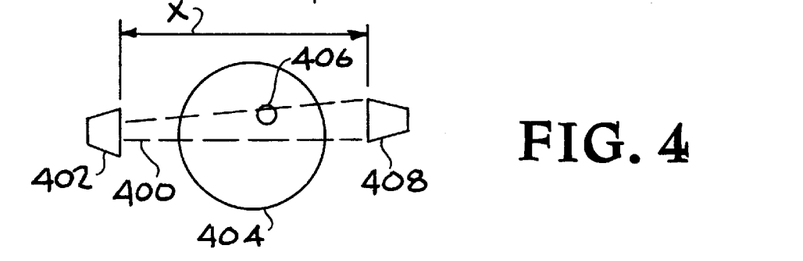
FIG. 4 shows a diagram of the TOF geometry.

Since only TOF data is of interest, which differs from that of a normal sample (and the normal sample time delays actually cause confusion in the signal—see FIG. 4), the processed normal signals
$S_i^\theta(t)_{norm}$ are used to, in effect, filter the measured processed signals before reconstructing the map. This can be done most simply by calculating a new signal $D_i^\Theta(t)$ for each receiver, where $D_i^\Theta(t) = S_i^\Theta(t)_{meas} - S_i^\Theta(t)_{norm}$ There are many other possible filter methods which could be used (and may be better) based on the processed normal signal, including a simple cut-off for time delays within the same range as those found in the processed normal signal.

The data set $D_i^\Theta(t)$ can then be reconstructed to form the map of the sample by means of a standard tomographic back projection method.

Figure 5A:
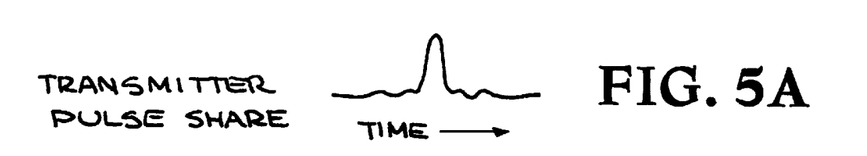
FIGS. 5A–C respectively show sketches of the transmitted pulse waveform, and the received signals without and with a blood pool in the path between the transmitter and one receiver element.
Figure 5B:
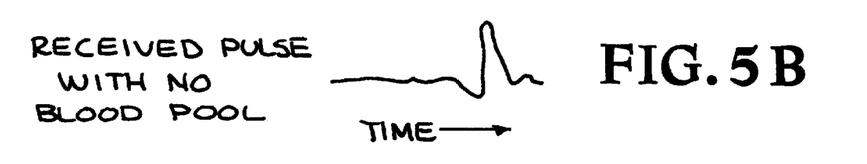
Figure 5C:
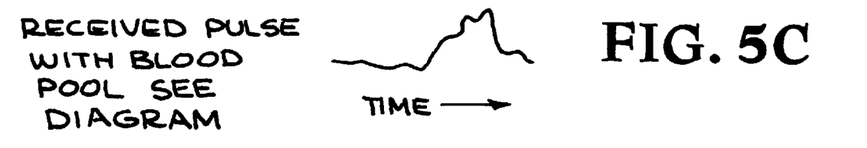

FIG. 4 shows a diagram of the TOF geometry. A beam 400 from transmitter 402 passes through a sample 404 with a blood pool or dielectric anomaly 406 and is received by receiver 408. FIGS. 5A–C respectively show sketches of the transmitted pulse waveform, and the received signals without and with a blood pool in the path between the transmitter and one receiver element.

Examples of the radar transmitters, receivers and microwave electronics usable in the present invention are described in U.S. Pat. No. 5,757,320 titled "Short Range, Ultra-Wideband Radar with High Resolution Swept Range Gate" which is incorporated herein by reference. Separate MIR transmitter and receiver boards can be used for transmission mode measurements.

An example of a data acquisition system that is usable in the present invention is the Laptop PC Pentium II processor, large hard disk ~4 gigabytes with 128 Mb of RAM and PCMCIA type II slot and color monitor with 600×800 pixels (or better) active matrix display.

Signal acquisition can be done using a National Instruments DAQ 700 or DAQ 1200 PCMCIA card. This provides both digital I/O for control and triggering of microwave levels as well as A/D conversions in multiple channels (up to 8) with a max sampling frequency of 100 kHz.

MIR rangefinder electronics put out range sweep signals at a rate of one full sweep at 40 Hz. Therefore, if values at 256 points along each range sweep are taken at 40 Hz, then the sampling rate will be $$\frac{256}{1/40 \text{ sec}} \approx 10 \text{ kHz per channel.}$$

The NI DAQ700 or 1200 (100 kHz sampling rate over all channels) can easily handle four channels simultaneously sweeping, or could just sweep each channel independently and multiplex.

Data acquisition software and user interface can be written in LabView running under MS Windows 95 or 98. This includes a GUI which allows the user to calibrate the system, test system operation and hardware, run a scan on a patient, display and manipulate the reconstructed head map and store and/or download patient data, all using simple buttons on the GUI. In addition, a post-processing algorithm which is applied to the reconstructed map can be incorporated to highlight suspect regions in the head map.

Figure 6:
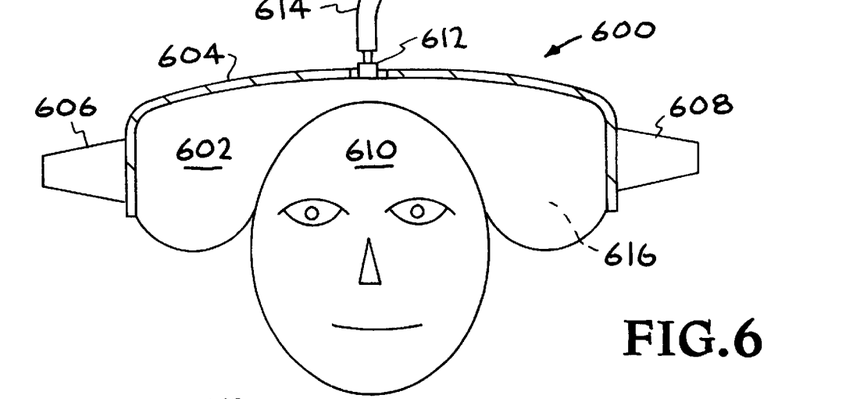
FIG. 6 shows the dielectric helmet placed on a patient's head.

The dielectric helmet 600 insert shown in FIG. 6 includes a helmet insert 602 comprising a firm, but stretchable plastic bag (also shown in FIG. 7) having a shape which, when filled with dielectric matching fluid, is designed to fit snugly both within the device housing 604 (to which the antennas 606, 608 are mounted) and over the patient's head 610.

Figure 7:
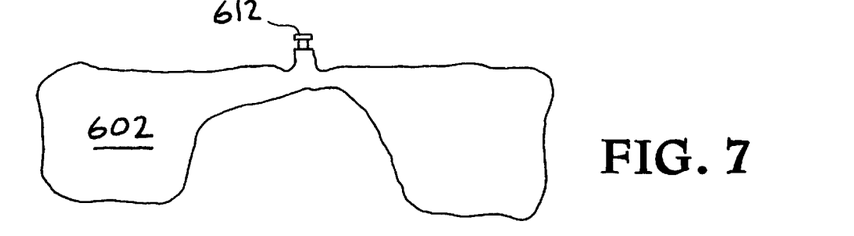
FIG. 7 shows a helmet insert in an unpressurized condition.

Helmet insert 602 is meant to be a disposable, single use item in order maintain patient hygiene. The purpose of the helmet insert is primarily to serve as a dielectric matching medium between the antennas and the patient's head, thus providing a uniform medium into which the microwave radiation is launched which, in turn, minimizes reflections at interfaces. In addition, the helmet insert comfortably immobilizes and positions the patient's head at the center of the device during data acquisition. The helmet insert must be made of a material which can stretch and expand to fill the housing, and conform to the patient's head without leaving gaps, yet it must roughly maintain it's shape. FIG. 7 shows a helmet insert 602 in an unpressurized condition. The helmet insert includes a helmet inlet quick disconnect 612, which is connected to a dielectric liquid fill tube 614 through which dielectric filling liquid 616 is input to the helmet insert 602 from a reservoir (not shown). Helmet insert 602 must be made of a material having the same (or nearly the same) refractive index (in the microwave band being used) as the dielectric filling liquid. One possible material is silicone rubber impregnated with $TiO_2$ (or other) particles which have a high refractive index. The refractive index of the helmet insert can then be tuned by adjusting the density of the particles within the silicone rubber.

The helmet insert is formed to its initial shape, which may be a right cylinder with an approximately hemispherical indentation, to accommodate the patient's head on one side and protruding into the cylinder about ¾ of its height. Helmet inserts can be pre-fabricated for several ranges of patient head sizes, and a quick measuring gauge may also be provided so that the operator can quickly determine which size insert to use for a particular patient.

At the top and center of the helmet insert 602 is an inlet spigot for the dielectric filling liquid. This inlet has a quick disconnect 612, as discussed above, with an internal valve which mates with a similar one on the dielectric liquid filling tube. Once formed in the manufacturing process, the helmet inserts are fitted with the inlet spigots and then pumped out to a "rough" vacuum ($\sim 10^{-3}$ torr) in order to remove any air which will form bubbles, and therefore gaps, in the dielectric filling. The inserts are provided evacuated and individually wrapped and sealed in an outer plastic bag. When used, each is filled before each use from a reservoir containing prepared dielectric filling fluid (having the correct dielectric properties) through the filling tube which connects to the spigot on the helmet insert. Since they come evacuated, each insert is first unwrapped, then snapped (a snap ring at the base of the spigot secures the insert) into the housing with the spigot protruding through a hole in the top of the housing. The fill tube is then connected, and the insert is then pre-filled until it begins to take it's proper shape and is slightly firm. Next the patient's head is placed into the opening in the insert, and the insert is pressurized until a snug fit is obtained at all interface surfaces (housing and patient's head). The device is now ready to acquire data. Once data acquisition is complete, the insert is removed from the housing, the filling liquid is drained for re-use and the insert itself is discarded.

Possible index matching materials include the following:
1) Water doped with microballoons or oil emulsion;
2) Gelatin doped with salt or oils to raise or lower nr;
3) Silicone doped with water globules or other high nr;
4) Plastics doped with $TiO_2$ powder;
5) Silicone doped with $TiO_2$ or other high nr material; and
6) Open cell foam impregnated with gelatin.

The density of dopant, type of doping material and dopant particle size can be varied in order to tune dielectric properties of the filling material. Materials will be chosen for flexibility or stiffness and/or stability (won't rot or change properties).

Figure 8:
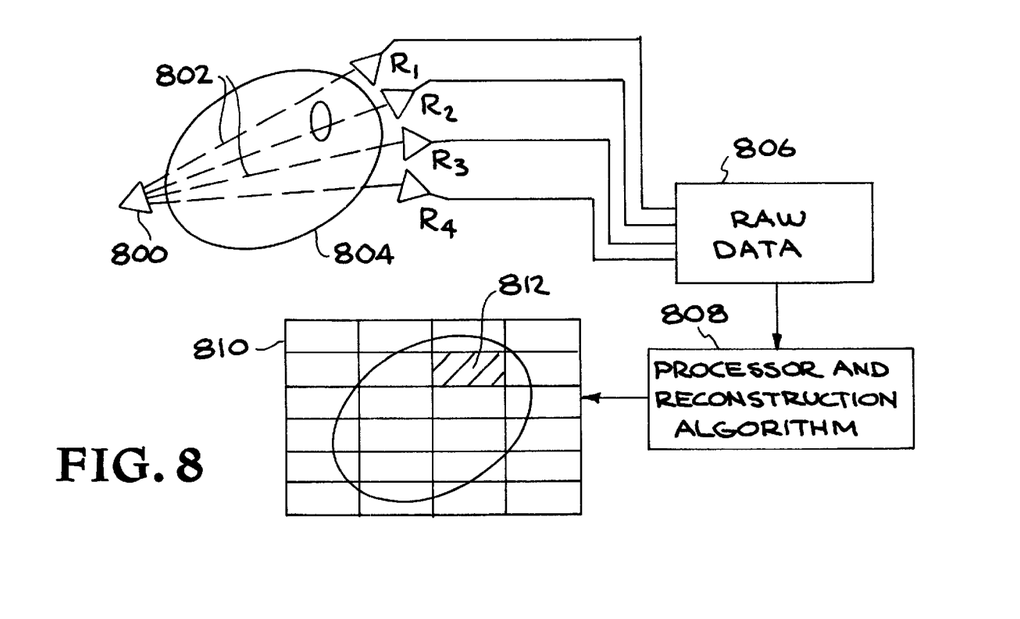
FIG. 8 shows a reconstructed map of the head showing the region containing a hemorrhage.

FIG. 8 depicts a system that converts raw or pre-processed (see description of algorithm above) data into a map of the head which indicates the hemorrhaging region. A transmitter antenna 800 projects a transmitted pulse shown by dotted lines 802 through the head 804 to receiver antennas $R_1$, $R_2$, $R_3$ and $R_4$. A processor, which includes a standard reconstruction algorithm 808 converts the data 806 from $R_1$, $R_2$, $R_3$ and $R_4$ into a reconstructed map 810 of the head showing the region 812 containing the hemorrhage.

Changes and modifications in the specifically described embodiments can be carried out without departing from the scope of the invention, which is intended to be limited by the scope of the appended claims.

What is claimed is:

1. A microwave hemorrhage detector, comprising:
   means for producing a pulsed microwave signal, wherein said microwave signal is transmitted across a medium selected from a group consisting of a portion of a human body and a portion of an animal body to produce a transmitted signal;
   means for detecting said transmitted signal to produce a detected signal; and
   means for analyzing said microwave signal and said detected signal to determine whether a hemorrhage exists within said medium, wherein said microwave signal and said detected signal are analyzed to produce a value selected from the group consisting of the real part of the refractive index and the loss due to absorption.

2. The microwave hemorrhage detector of claim 1, wherein said means for producing a microwave signal comprise at least one microwave transmitter.

3. The microwave hemorrhage detector of claim 2, wherein said at least one microwave transmitter is capable of producing microwave pulses having a pulse duration within a range of 60 ps to 120 ps and having a center frequency within a range of 2 Hz to 5 GHz.

4. The microwave hemorrhage detector of claim 3, wherein said at least one microwave transmitter includes a wide angle horn transmitter.

5. The microwave hemorrhage detector of claim 1, wherein said means for detecting said transmitted signal comprise at least one microwave receiver antenna.

6. The microwave hemorrhage detector of claim 5, wherein said at least one microwave receiver antenna is capable of receiving microwave pulses having a pulse duration within a range of 60 ps to 120 ps and having a center frequency within a range of 2 Hz to 5 GHz.

7. The microwave hemorrhage detector of claim 6, wherein said at least one microwave receiver antenna comprises an array of at least 4 receiver antennas mounted with a gap of 3 to 5 mm between them, wherein said gap comprises microwave absorbing material to help reduce any residual crosstalk between antennas.

8. The microwave hemorrhage detector of claim 5, wherein said at least one microwave receiver antenna comprises a wide angle horn antenna.

9. The microwave hemorrhage detector of claim 1, further comprising a housing, wherein said means for producing a microwave signal comprise at least one microwave transmitter, wherein said means for detecting said transmitted signal comprise at least one microwave receiver antenna, wherein said at least one microwave transmitter and said at least one microwave receiver antenna are fixedly and operatively mounted to said housing.

10. The microwave hemorrhage detector of claim 9, wherein said housing comprises microwave absorber material.

11. The microwave hemorrhage detector of claim 10, wherein said microwave absorber material provides shielding, prevents entry of signals from outside objects, reduces residual crosstalk within said means for producing a microwave signal and reduces residual crosstalk within said means for detecting said transmitted signal.

12. The microwave hemrrorhage detector of claim 11, wherein said housing further comprises a helmet insert.

13. The microwave hemorrhage detector of claim 12, wherein said helmet insert comprises a bag designed to fit within said housing and over a patient's head.

14. The microwave hemorrhage detector of claim 13, wherein said bag is filled with dielectric material.

15. The microwave hemorrhage detector of claim 14, wherein said bag comprises a material which can stretch and expand to fill said housing and conform to said patient's head.

16. The microwave hemorrhage detector of claim 15, wherein said helmet insert further comprises an inlet quick disconnect to enable said helmet insert to be connected to a dielectric liquid fill tube through which dielectric filling liquid may be input to said helmet insert.

17. The microwave hemorrhage detector of claim 16, wherein said helmet insert comprises material having about the same refractive index, in the microwave band being used, as said dielectric liquid.

18. The microwave hemorrhage detector of claim 17, wherein said helmet insert comprises silicone rubber impregnated with $TiO_2$.

19. The microwave hemorrhage detector of claim 17, wherein said helmet insert comprises silicone rubber impregnated with particles which have a refractive index that is high enough to adjust the refractive index of said silicon rubber such that said helmet insert comprises material having about the same refractive index, in the microwave band being used, as said dielectric liquid, wherein the refractive index of said helmet insert can then be tuned by adjusting the density of the particles within the silicone rubber.

20. The microwave hemorrhage detector of claim 17, wherein said helmet insert serves as a dielectric matching medium between said means for producing a microwave signal, said means for detecting said transmitted microwave signal and said patient's head, thus providing a uniform medium into which the microwave radiation is launched which, in turn, minimizes reflections at interfaces.

21. The microwave hemorrhage detector of claim 17, wherein said helmet insert immobilizes and positions said patient's head at the center of said microwave hemorrhage detector while it is analyzing said microwave signal and said detected signal to determine whether a hemorrhage exists.

22. The microwave hemorrhage detector of claim 14, wherein said dielectric material is selected from a group consisting of water doped with microballoons or oil emulsion, gelatin doped with salt or oils to raise or lower $n_r$, silicone doped with water globules or other high $n_r$, plastics doped with $TiO_2$ powder, silicone doped with $TiO_2$ or other high nr material, and open cell foam impregnated with gelatin.

23. The microwave hemorrhage detector of claim 14, wherein said dielectric material comprises a dopant, wherein the density, type and particle size of said dopant can be varied in order to tune dielectric properties of said dielectric material.

24. The microwave hemorrhage detector of claim 9, wherein said at least one microwave transmitter and said at least one microwave receiver antenna rotates about an axis of rotation of said housing.

25. The microwave hemorrhage detector of claim 1, further comprising a housing, wherein said means for producing a microwave signal comprise a plurality of microwave transmitter/receiver units fixedly and operatively mounted to said housing, wherein said detector further comprises means for electronically multiplexing said plurality of microwave transmitter/receiver units such that microwave signals are transmitted and received in a selected pattern about an axis of rotation of said housing.

26. The microwave hemorrhage detector of claim 1, wherein said means for analyzing said microwave signal and said detected signal comprises a reconstruction algorithm which analyses said microwave signal and said detected signal to determine whether a hemorrhage exists within said medium.

27. The microwave hemorrhage detector of claim 1, further comprising a contrast agent comprising microbubbles, wherein said contrast agent is inserted into said medium to increase the difference between the index of refraction between a hemorrhage and said medium.

28. A method for determining whether a hemorrhage exists within a medium, comprising:
producing a pulsed microwave signal;
transmitting said microwave signal through a medium selected from a group consisting of a portion of a human body and a portion of an animal body to produce a transmitted signal;
detecting said transmitted signal after it has passed through said medium to produce a detected signal; and
analyzing said microwave signal and said detected signal to determine whether a hemorrhage exists within said medium, wherein said microwave signal and said detected signal are analyzed to produce a value selected from the group consisting of the real part of the refractive index and the loss due to absorption.

29. The method of claim 28, wherein said microwave signal is transmitted through said medium at a plurality of angles, wherein the step of analyzing said microwave signal and said detected signal is carried out with a reconstruction algorithm.

30. The method of claim 29, wherein said reconstruction allgorithn comprises taking the integral of the refractive index at all points along the path traveled by said microwave signal and said transmitted signal between the transmitter and receiver and reconstructing an image from a set of path integrals.

31. The method of claim 29, wherein said transmitted signal comprises a pulse shape, wherein said reconstruction algorithm comprises:
suppressing the effects of said pulse shape of said transmitted signal in each said detected signal;
calculating a normal signal;
storing said normal signal in the memory of a controlling computer system; and
reconstructing a data set from said normal signal to form a map of said medium by means of a standard tomographic back projection method.

32. The method of claim 31, further comprising applying a post-processing algorithm to said map to highlight hemorrhage regions in a head map.

33. The method of claim 30, further comprising inserting a contrast agent comprising microbubbles into said medium to increase the difference between the index of refraction between a hemorrhage and said medium.

34. An apparatus, comprising:
means for producing a microwave signal, wherein said microwave signal is transmitted through a medium selected from a group consisting of a portion of a human body and a portion of an animal body to produce a transmitted signal;
means for detecting said transmitted signal to produce a detected signal; and
means for analyzing said microwave signal and said detected signal to determine the index of refraction, at the wavelength of said microwave signal, of selected points within said medium.

35. The apparatus of claim 34, wherein said means for producing a microwave signal comprise at least one microwave transmitter.

36. The apparatus of claim 35, wherein said at least one microwave transmitter is capable of producing microwave pulses having a pulse duration within a range of 60 ps to 120 ps and having a center frequency within a range of 2 Hz to 5 GHz.

37. The apparatus of claim 36, wherein said at least one microwave transmitter includes a wide angle horn transmitter.

38. The apparatus of claim 34, wherein said means for detecting said transmitted signal comprise at least one microwave receiver antenna.

39. The apparatus of claim 38, wherein said at least one microwave receiver antenna is capable of receiving microwave pulses having a pulse duration within a range of 60 ps to 120 ps and having a center frequency within a range of 2 Hz to 5 GHz.

40. The apparatus of claim 38, wherein said at least one microwave receiver antenna comprises an array of at least 4 receiver antennas mounted with a gap of 3 to 5 mm between them, wherein said gap comprises microwave absorbing material to help reduce any residual crosstalk between antennas.

41. The apparatus of claim 38, wherein said at least one microwave receiver antenna comprises a wide angle horn antenna.

42. The apparatus of claim 34, further comprising a housing, wherein said means for producing a microwave signal comprise at least one microwave transmitter, wherein said means for detecting said transmitted signal comprise at least one microwave receiver antenna, wherein said at least one microwave transmitter and said at least one microwave receiver antenna are fixedly and operatively mounted to said housing.

43. The apparatus of claim 42, wherein said housing comprises microwave absorber material.

44. The apparatus of claim 43, wherein said microwave absorber material provides shielding, prevents entry of signals from outside objects, reduces residual crosstalk within said means for producing a microwave signal and reduces residual crosstalk within said means for detecting said transmitted signal.

45. The apparatus of claim 44, wherein said housing further comprises a helmet insert.

46. The apparatus of claim 45, wherein said helmet insert comprises a bag designed to fit within said housing and over a patient's head.

47. The apparatus of claim 46, wherein said bag is filled with dielectric material.

48. The apparatus of claim 47, wherein said bag comprises a material which can stretch and expand to fill said housing and conform to said patient's head.

49. The apparatus of claim 48, wherein said helmet insert further comprises an inlet quick disconnect to enable said helmet insert to be connected to a dielectric liquid fill tube through which dielectric filling liquid may be input to said helmet insert.

50. The apparatus of claim 49, wherein said helmet insert comprises material having about the same refractive index, in the microwave band being used, as said dielectric liquid.

51. The apparatus of claim 50, wherein said helmet insert comprises silicone rubber impregnated with $TiO_2$.

52. The apparatus of claim 50, wherein said helmet insert comprises silicone rubber impregnated with particles which have a refractive index that is high enough to adjust the refractive index of said silicon rubber such that said helmet insert comprises material having about the same refractive index, in the microwave band being used, as said dielectric liquid, wherein the refractive index of said helmet insert can then be tuned by adjusting the density of the particles within the silicone rubber.

53. The apparatus of claim 50, wherein said helmet insert serves as a dielectric matching medium between said means for producing a microwave signal, said means for detecting said transmitted microwave signal and said patients head, thus providing a uniform medium into which the microwave radiation is launched which, in turn, minimizes reflections at interfaces.

54. The apparatus of claim 50, wherein said helmet insert immobilizes and positions said patient's head at the center of said microwave hemorrhage detector while it is analyzing said microwave signal and said detected signal to determine whether a hemorrhage exists.

55. The apparatus of claim 47, wherein said dielectric material is selected from a group consisting of water doped with microballoons or oil emulsion, gelatin doped with salt or oils to raise or lower $n_r$, silicone doped with water globules or other high $n_r$, plastics doped with $TiO_2$ powder, silicone doped with $TiO_2$ or other high $n_r$ material, and open cell foam impregnated with gelatin.

56. The apparatus of claim 47, wherein said dielectric material comprises a dopant, wherein the density, type and particle size of said dopant can be varied in order to tune dielectric properties of said dielectric material.

57. The apparatus of claim 42, wherein said at least one microwave transmitter and said at least one microwave receiver antenna rotates about an axis of rotation of said housing.

58. The apparatus of claim 34, further comprising a housing, wherein said means for producing a microwave signal comprise a plurality of microwave transmitter/receiver units fixedly and operatively mounted to said housing, wherein said detector further comprises means for electronically multiplexing said plurality of microwave transmitter/receiver units such that microwave signals are transmitted and received in a selected pattern about an axis of rotation of said housing.

59. The apparatus of claim 34, wherein said means for analyzing said microwave signal and said detected signal comprises a reconstruction algorithm which analyses said microwave signal and said detected signal to determine whether a hemorrhage exists within said medium.

60. The apparatus of claim 34, further comprising a contrast agent comprising microbubbles, wherein said contrast agent is inserted into said medium to increase the difference between the index of refraction between a hemorrhage and said medium.

* * * * *